United States Patent [19]

Jennings et al.

[11] Patent Number: 4,699,780

[45] Date of Patent: Oct. 13, 1987

[54] COSMETIC COMPOSITION

[75] Inventors: Deborah J. Jennings; Thomas J. Vichroski, both of Oakdale, N.Y.

[73] Assignee: Estee Lauder Inc., New York, N.Y.

[21] Appl. No.: 738,772

[22] Filed: May 29, 1985

[51] Int. Cl.$^4$ .................. A61K 7/025; A61K 7/027; A61K 7/42; A61K 7/44

[52] U.S. Cl. .................. 424/60; 424/DIG. 5; 424/59; 424/63; 424/64

[58] Field of Search ............... 424/59, 60, 69, DIG. 5, 424/64

[56] References Cited

U.S. PATENT DOCUMENTS

| | | | |
|---|---|---|---|
| 2,230,063 | 1/1941 | Klimist | 424/64 |
| 2,649,382 | 8/1953 | Vesce | 424/64 |
| 2,839,482 | 6/1958 | Geen et al. | 524/269 |
| 2,876,162 | 3/1959 | Lauffer | 424/64 |
| 2,937,129 | 5/1960 | Garwood | 208/18 |
| 3,086,914 | 4/1963 | Solloway | 424/64 |
| 3,088,876 | 5/1963 | Buth | 424/64 |
| 3,151,181 | 9/1964 | Hewitt et al. | 585/18 |
| 3,201,314 | 8/1965 | Morhauser et al. | 424/64 |
| 3,211,619 | 10/1965 | Buchwalter et al. | 424/DIG. 5 |
| 3,344,204 | 9/1967 | Clough et al. | 585/18 |
| 3,489,690 | 1/1970 | Lachampt et al. | 424/64 |
| 3,592,910 | 7/1971 | Clark et al. | 424/300 |
| 3,641,239 | 2/1972 | Mohrlok | 424/64 |
| 3,642,635 | 2/1972 | MacLeod | 252/59 |
| 3,876,722 | 4/1975 | Rossi et al. | 585/18 |
| 4,367,220 | 1/1983 | Boulogne et al. | 424/64 |
| 4,372,944 | 2/1983 | Herrold | 424/83 |
| 4,425,364 | 1/1984 | Vanlerberghe et al. | 424/64 |

FOREIGN PATENT DOCUMENTS 0132631  2/1985  European Pat. Off. ............. 424/63

OTHER PUBLICATIONS

Finnemore, Essential Oils, 1932, p. 502.
Vol. 6, *Kirk–Othmer Encyclopedia of Chemical Technology*, John Wiley & Sons, Inc., (1965), pp. 355, 356, 371, 374, 375.
Vol. One, *Modern Cosmeticology*, J. B. Wilkinson et al., Chemical Publishing Co., Inc., New York, (1962), pp. 614–625.
Vol. 1, *Cosmetics Science and Technology*, Balsam et al., Wiley–Interscience, New York, (1972), pp. 241–305.
*CTFA Cosmetic Ingredient Dictionary*, (Third Edition) 1982, The Cosmetic Toiletry and Fragrance Association, Inc., Washington, D.C. 20005, p. 126.

*Primary Examiner*—Dale R. Ore
*Attorney, Agent, or Firm*—Richard M. Barnes

[57] ABSTRACT

Disclosed is a cosmetic composition comprising a resin, a polysiloxane, a polyolefin that is fluid at room temperature, and at least one hardening agent. Suitable coloring materials include dyes, pigments and pearling agents. The compositions of the present invention may be molded into the shape of a lipstick. They may also be applied in the form of a cream, especially when the composition is intended to be used as a lip gloss or as a lip balm.

24 Claims, No Drawings

COSMETIC COMPOSITION

FIELD OF THE INVENTION

This invention relates to a new cosmetic composition for use as a lipstick, as a lip balm or as an undercoat or overcoat for use with other lip cosmetics.

BACKGROUND OF THE INVENTION

Lipstick is one of the most widely used cosmetics. Formulating a new commercially practicable lipstick composition can be a difficult task because the composition must satisfy a number of criteria. In particular, a commercial lipstick composition should have most (if not all) of the following characteristics:

(a) it should be free from discoloration, specks of grit, pinholes and other imperfections;

(b) it should have a desirable consistency;

(c) it should not be too dry or brittle and at the same time oil droplets should not form on its surface;

(d) the composition should have a high enough melting point to assure that it does not melt under hot storage conditions (e.g., in a purse left in the sun) and that it is sufficiently hard and strong to enable it to be molded into stick form and to withstand normal use without breaking;

(e) it should be soft enough so that it can be easily applied to the lips;

(f) it should have a pleasant taste and odor or it should be tasteless and odorless; and (g) it should have desirable film forming properties, e.g., films formed from the composition should be free from tackiness and have an emollient feel without imparting a sensation of dryness, and the resulting film should be durable.

In addition to the foregoing characteristics, an important criterion is that there should be little or no tendency for the coloring materials in the lipstick to migrate to the edges of the lips and onto the surrounding skin. Such migration, when it occurs, is known as "feathering."

SUMMARY OF THE INVENTION

The present invention is directed to a cosmetic composition comprising (a) a resin selected from the group consisting of:
(i) resins formed by the polymerization of the monomers beta-pinene, dipentene alpha-pinene, d-limonene or l-limonene, or mixtures of said monomers; and
(ii) the pentaerythritol or glycerol esters of polymerized tall oil rosin, polymerized wood rosin, polymerized hydrogenated rosin, or polymerized mixtures of said rosins; said resin having a softening point between about 10 and about 130° C. (the preferred resins being those of item (i) above and a most preferred resin being one formed by polymerization of dipentene), the higher softening point materials (i.e. those materials softening at about 90° C. or above) being optionally diluted with a hydrocarbon that is a liquid at room temperature (preferably a nonvolatile hydrocarbon, and more preferably mineral oil) that serves as a processing aid to make it easier to mix the resin with the other components of the composition at a somewhat lower temperature than would otherwise be required, the resin-diluent combinations comprising up to about 60 percent by weight of diluent (based on the total amount of said resin and said hydrocarbon in the combination), preferably about 20 to about 60 percent by weight of diluent, and more preferably about 40 to about 60 percent by weight of diluent;

(b) a polysiloxane selected from the group consisting of polydimethylsiloxane, polydiethylsiloxane, polyethylmethylsiloxane, phenyltrimethylpolysiloxane and polydimethylcyclosiloxane, and mixtures thereof, said polysiloxane (or the mixtures thereof) having a viscosity of at least about 5 centistokes at 25 ° C.;

(c) a polyolefin that is fluid at room temperature, said polyolefin having an average molecular weight of from about 1300 to about 2500, more preferably about 1500, said polyolefin having
(i) a density (ASTM D-1168) at 75° F. of about 0.7 to about 1.0, preferably about 0.8 to about 0.9, more preferably about 0.84 to about 0.88 and most preferably about 0.86;
(ii) a pour point (ASTM D-97) of less than $-30°$ F.;
(iii) an iodine number (ASTM D-1959) of about 27 to about 33, preferably about 29 to about 31, and most preferably about 30; and
(iv) a viscosity (ASTM D-3236) at 37.8° C. of about 18 to about 6400 centistokes, preferably about 400 to about 1000 centistokes, and most preferably about 530 centistokes; and (d) at least one hardening agent selected from the group consisting of paraffins having melting points from about 45 to about 120° C., microcrystalline waxes having melting points from about 60 to about 95° C. and hydrocarbon waxes having melting points from about 25° C. to about 135° C.

For the sake of brevity, hereinafter in this specification the components of our invention are sometimes referred to as a "resin", a "polysiloxane", a "polyolefin", and a "hardening agent".

The cosmetic composition of our invention may be formulated into a lipstick having a combination of desirable properties, including little or no tendency to feather. The composition of our invention may also be used as a lip balm, or as an undercoat or overcoat for use with other lip cosmetics.

When the cosmetic composition of the present invention is used as a lipstick, it will usually contain at least one compatible coloring material. Such coloring material may be omitted, however, for certain applications, e.g., when the composition is used as an undercoat or overcoat. When used as an undercoat or an overcoat, the composition of our invention will minimize (if not prevent altogether) the tendency to feather of colored lip products that are applied over it or under it.

The compositions of the present invention preferably are molded into the shape of a lipstick, but they may also be applied in the form of a cream, especially when used as a lip gloss or as a lip balm.

DESCRIPTION OF PREFERRED EMBODIMENTS

In a preferred embodiment, the cosmetic composition of our invention comprises:

(a) about 0.2 to about 2.0 parts by weight of a resin;
(b) about 10 to about 25 parts by weight of a polysiloxane;
(c) about 25 to about 40 parts by weight of a polyolefin;

(d) about 5 to about 30 parts by weight of a hardening agent;

(e) 0 to about 40 parts by weight of at least one coloring material (the coloring material optionally including a vehicle); and (f) 0 to about 16 parts by weight of other ingredients that are conventionally used in compositions to be applied to the lips (hereinafter, referred to as conventional ingredients).

In a more preferred embodiment, the cosmetic composition of our invention comprises:

(a) about 0.4 to about 2.0 parts by weight of a mixture of a combination of (i) a resin having a softening point of about 100° C. to about 125° C., and (ii) a hydrocarbon that is a liquid at room temperature (more preferably, a non-volatile hydrocarbon, and most preferably, mineral oil), the hydrocarbon being present in an amount from about 20 to about 60 percent by weight based on the total amount of said resin and said hydrocarbon in the combination;

(b) about 10 to about 25 parts by weight of a polysiloxane;

(c) about 25 to about 40 parts by weight of a polyolefin;

(d) about 5 to about 30 parts by weight of a hardening agent, said hardening agent comprising 0 to 100 percent by weight of Fischer-Tropsch wax with a melting point of about 72 to about 78° C. and 100 to 0 percent by weight of a mixture of microcrystalline waxes, said mixture of microcrystalline waxes having a melting point of about 75 to about 76° C. (more preferably about 75.5° C.);

(e) 0 to about 40 parts by weight of at least one coloring material (the coloring material including a vehicle, if necessary); and (f) 0 to about 16 parts by weight of conventional ingredients.

In a particularly preferred embodiment, the cosmetic composition of this invention comprises:

(a) about 0.75 to about 1.25 parts by weight of a resin having a softening point of about 115° C. and mineral oil, the mineral oil being present in an amount from about 40 to about 60 percent by weight, based on the total amount of the resin and the mineral oil in the composition;

(b) about 14 to about 20 parts by weight of phenylmethylpolysiloxane having a viscosity of about 22.5 centistokes at 25° C.;

(c) about 30 to about 35 parts by weight of a polyolefin, said polyolefin having a viscosity of about 530 centistokes at 37.8° C., an iodine number of about 30, a pour point of less than −30° F., and a density at 75° F. of about 0.86;

(d) about 18 to about 24 parts by weight of a hardening agent, said hardening agent comprising a blend of about 40 to about 60 percent by weight of Fischer-Tropsch wax with a melting point of about 72 to about 78° C. and about 60 to about 40 percent by weight of a mixture of microcrystalline waxes having a melting point of about 75.5° C.;

(e) about 8 to about 12 parts by weight of pigment;

(f) about 14 to about 23 parts by weight of a pigment vehicle comprising squalane and octyl dodecanol; and (g) about 0.1 to about 1.5 parts by weight of conventional ingredients (e.g., perfume, a preservative containing about 1 part by weight of butyl paraben for 3 parts by weight of propyl paraben, a sunscreen, an antioxidant and mixtures of such ingredients).

The ingredients used in the composition of this invention should be of a quality or purity (such as U.S.P. or N.F.) suitable for cosmetic use and should be compatible when used together in a particular composition. Unless indicated otherwise, the physical properties of the components of the composition of the present invention specified herein are the properties of those components before they are mixed with the composition's other components.

Suitable resins that may be used in the composition of the present invention include the Zonarez® B, Zonarez 7000, Zonarez M-1115, Zonarez alpha 25, Zonatac® and Zonester® series of resins available from Arizona Chemical Company, Fairlawn, N.J., as well as the Foral®, Pentalyn®, Regalrez®, Hercolyn®, and Piccolyte® series of resins available from Hercules, Inc., Wilmington, Del.

Among the suitable polysiloxanes are the Dow Corning® 200 Fluid Series and the Dow Corning® 225, 244, 245, 344, 345, and 556 fluids available from Dow Corning Corporation, Midland, Mich., as well as SWS-101, F-212, and F-575 silicone fluids available from SWS Silicones Corporation, Adrian, Mich.

The polyolefin that is used in our invention is a polymer having a small degree of unsaturation (i.e., it has a relatively low iodine number) and is highly branched (i.e., it has a relatively high average molecular weight for a liquid). A particularly preferred polyolefin polymer is Vybar® 825, available from the Bareco Division, Petrolite Corporation, Tulsa, Ok.

Suitable hardening agents include: semirefined, full refined and/or synthetically derived paraffins with melting points from about 45 to about 120° C. (for example, the Aristowax® series available from Union Oil of California, San Francisco, Calif., the Eskar® series manufactured by the Amoco Oil Company, Chicago, Ill. and the Parvan® series available from Exxon Company, Houston, Tex.), microcrystalline waxes with melting points from about 60 to about 95° C. (for example, the Be Square® series from the Bareco Division of Petrolite Corporation and the Multiwax® series from Witco Chemical Corporation, Sonneborn Division, New York, N.Y.) and certain synthetically derived, modified hydrocarbon waxes, such as the Vestowaxes®, Duroxon® waxes, and Efton® waxes available from Durachem, Dura Commodities Corporation, Harrison, N.Y. Combinations of the foregoing hardening agents may be used in our composition. The hardening agents are used in amounts sufficient to (a) provide the proper hardness so that our cosmetic composition can be formed into a stick, and (b) provide a texture that is smooth and uniform and enables the composition to be deposited smoothly on the lips when the stick is applied to the lips.

Virtually all (if not all) of the coloring materials and pearling agents presently used in commercial lipstick compositions are suitable for use in the compositions of the present invention. Among these are the lakes of FD&C Red #3, D&C Red #3, D&C Red #6, D&C Red #7, D&C Red #21, D&C Red #27, D&C Red #30, D&C Red #33, D&C Red #36, D&C Red #40, D&C Orange #5, FD&C Yellow #5, FD&C Yellow #6, D&C Yellow #6, D&C Yellow #10, FD&C Blue #1, D&C Blue #1, iron oxides, carmine, mica, titanium dioxide, titanium dioxide coated mica, bismuth oxychloride, guanine, zinc oxide, talc and kaolin. Two or more suitable coloring materials may be mixed to provide a desired shade.

If a vehicle for our composition's coloring material is used, it must be compatible with the other components of the composition, i.e., it must be miscible with or soluble in the components and it should not synerize (sweat) on the surface of the finished product. Among such suitable vehicles are squalane, isopropyl myristate, butyl stearate, decyl oleate, isopropyl palmitate, 2-ethyl hexylstearate, oleyl alcohol, octyl dodecanol, isocetyl alcohol and erucyl erucate. A mixture of suitable vehicles may also be used.

One or more of a number of conventional ingredients may be included in the compositions of the present invention. Such ingredients include perfumes; sunscreens, such as PABA and its derivatives; anti-oxidants, such as the propyl, octyl and dodecyl esters of gallic acid, butylated hydroxyanisole, butylated hydroxytoluene, tocopherol and ascorbyl palmitate; preservatives, such as butyl paraben, propyl paraben and ethyl paraben; and other ingredients such as mink oil and hydrolyzed animal protein.

It should be understood that, as used herein, the term "resin" also includes mixtures of two or more resins and that, similarly, the term "polysiloxane" includes mixtures of two or more polysiloxanes, and the term "polyolefin" includes mixtures of two or more polyolefins.

The lipstick oomposition of our invention may be made by the techniques conventionally used to make lipstick compositions. In particular, the compositions of our invention may be made by the following steps:

(a) dispersing the composition's dyes and pigments (if any), and possibly some or all of the composition's pearling agents (if any), in a vehicle;

(b) passing the resulting dispersion through a three-roll mill or other suitable grinding equipment until the desired fineness-of-grind is obtained;

(c) melting the remaining ingredients of the composition, except any remaining pearling agents not milled and the composition's perfume (if any), together at a temperature several degrees above the highest melting point of any single ingredient;

(d) mixing the melted phase until it is uniform;

(e) adding the color dispersion obtained in step (b) (if the composition is colored) to the melted phase obtained in step (d);

(f) mixing the composition obtained in step (e), without permitting it to solidify;

(g) adding any additional pearling agents to the composition and mixing the resulting composition until it is uniform;

(h) adding any perfume that is desired to be in the composition and mixing the resulting composition until it is uniform;

(i) pouring the composition into conventional lipstick molds, allowing the composition to solidify, and unmolding the resulting lipsticks and placing them in suitable lipstick containers; and (j) if necessary, exposing the lipsticks to a very short period of intense heat to smooth over any minor surface imperfections.

A final product that contains no dyes or pigments, or that contains a dye but does not contain pigments, may not require processing with the three-roll mill or other grinding equipment.

The following non-limiting Examples illustrate the present invention.

EXAMPLES

EXAMPLE 1

A lipstick composition was prepared from the following ingredients in the specified amounts:

| Ingredient | Parts By Weight |
| --- | --- |
| Octyl dodecanol | 9.83 |
| Squalane | 5.00 |
| D&C Red #6 barium lake | 0.40 |
| D&C Red #7 calcium lake | 0.52 |
| FD&C Yellow #5 aluminum lake | 1.10 |
| Titanium Dioxide | 5.50 |
| D&C Red #27 aluminum lake | 1.00 |
| Mica | 3.00 |
| Pearling Agent (titanium dioxide coated mica) | 4.00 |
| Fischer-Tropsch wax, m.p. 72-78° C. | 9.00 |
| Vybar ® 825 (polyolefin) | 31.60 |
| Isostearoyl hydrolyzed animal protein | 0.40 |
| 1 to 1 mixture (parts by weight) of Multiwax ® W-445 and Multiwax ® W-835 (mixture of microcrystalline waxes with m.p. of 75.5° C.) | 12.00 |
| Butyl paraben | 0.05 |
| Propyl Paraben | 0.15 |
| Zonarez ® 7010 (51 parts by weight polyterpene resin (prepared from dipentene monomer)/49 parts by weight mineral oil, having a softening point of 10° C.) | 1.00 |
| Dow Corning ® 556 Fluid (phenylmethylpolysiloxane) | 15.00 |
| Tocopherol | 0.10 |
| Perfume | 0.35 |
| | 100.00 |

The above ingredients were mixed and processed as described in steps (a)–(j) above (passing a dispersion of the first nine ingredients through a three-roll mill) to prepare a product in the form of a lipstick.

EXAMPLE 2

A composition suitable for use as a lip balm, overcoat and undercoat and having the following composition was prepared:

| Ingredient | Parts By Weight |
| --- | --- |
| Vybar ® 825 | 56.80 |
| Fischer-Tropsch wax, m.p. 72-78° C. | 11.00 |
| 1 to 1 mixture (parts by weight) of Multiwax ® W-445 and Multiwax ® W-835 | 16.00 |
| Butyl paraben | 0.05 |
| Propyl Paraben | 0.15 |
| Zonarez ® 7010 | 1.00 |
| Dow Corning ® 556 Fluid | 15.00 |
| | 100.00 |

The above ingredients were mixed and processed as described in steps (c)–(j) above (but not processed on a three-roll mill) to prepare a product in the shape of a lipstick.

EXAMPLE 3

A lipstick having the following composition was prepared:

| Ingredient | Parts By Weight |
| --- | --- |
| Octyl dodecanol | 13.16 |
| Squalane | 5.00 |
| D&C Red #7 calcium lake | 0.66 |

-continued

| Ingredient | Parts By Weight |
|---|---|
| FD&C Blue #1 aluminum lake | 0.10 |
| Fischer-Tropsch wax, m.p. 72–78° C. | 9.00 |
| Vybar ® 825 | 30.53 |
| 1 to 1 mixture (parts by weight) of Multiwax ® W-445 and Multiwax ® W-835 | 14.00 |
| Butyl paraben | 0.05 |
| Propyl Paraben | 0.15 |
| Zonarez ® 7010 | 1.00 |
| Dow Corning ® 556 Fluid | 15.00 |
| Tocopherol | 0.10 |
| Bismuth oxychloride (pearling agent) | 11.00 |
| Perfume | 0.25 |
|  | 100.00 |

The above ingredients were mixed and processed as described in steps (a)–(j) above (passing a dispersion of the first four ingredients through a three-roll mill) to prepare a product in the form of a lipstick.

EXAMPLE 4 lipstick composition having the following composition was prepared:

| Ingredient | Parts By Weight |
|---|---|
| Octyl dodecanol | 14.30 |
| Squalane | 5.00 |
| D&C Red #6 barium lake | 0.60 |
| FD&C Yellow #5 aluminum lake | 0.30 |
| FD&C Blue #1 aluminum lake | 0.05 |
| Fischer-Tropsch wax, m.p. 72–78° C. | 8.00 |
| Octyldimethyl PABA | 10.00 |
| Vybar ® 825 | 27.70 |
| Isostearoyl hydrolyzed animal protein | 0.50 |
| 1 to 1 mixture (parts by weight) of Multiwax ® W-445 and Multiwax ® W-835 | 13.00 |
| Butyl paraben | 0.05 |
| Propyl Paraben | 0.15 |
| Zonarez ® 7010 | 15.00 |
| Dow Corning ® 556 Fluid | 1.00 |
| Tocopherol | 0.10 |
| Bismuth oxychloride (pearling agent) | 4.00 |
| Perfume | 0.25 |
|  | 100.00 |

The above ingredients were processed as described in steps (c)–(j) above (passing a dispersion of the first five ingredients through a three-roll mill) to prepare a product in the form of a lipstick.

We claim:
1. A cosmetic composition for the lips comprising:
   (a) a resin selected from the group consisting of
      (i) resins formed by the polymerization of the monomers beta-pinene, dipentene, alpha-pinene, d-limonene or l-limonene, or mixtures of said monomers, and
      (ii) the pentaerythritol or glycerol esters of polymerized tall oil rosin, polymerized wood rosin, polymerized hydrogenated rosin, and polymerized mixtures of said rosins; said resin having a softening point between about 10 and about 130° C.;
   (b) a polysiloxane selected from the group consisting of polydimethylsiloxane, polydiethylsiloxane, polyethylmethylsiloxane, phenyltrimethylpolysiloxane and polydimethylcyclosiloxane, and mixtures thereof, said polysiloxane having a viscosity of at least about 5 centistokes at 25° C.;
   (c) a polyolefin that is fluid at room temperature, said polyolefin having an average molecular weight of from about 1300 to about 2500, said polyolefin having
      (i) a density at 75° F. of about 0.7 to about 1.0;
      (ii) a pour point of less than −30° F.; and
      (iii) an iodine number of about 27 to about 33; and
      (iv) a viscosity at 37.8° C. of about 18 to about 6400 centistokes; and
   (d) at least one hardening agent selected from the group consisting of paraffins having melting points from about 45 to about 120° C., microcrystalline waxes having melting points from about 60° to about 95° C. and hydrocarbon waxes having melting points from about 25° C. to about 135° C.

2. The composition of claim 1, wherein component (a) is a resin having a softening point of above 90° C. and further wherein the composition contains a hydrocarbon that is liquid at room temperature, said hydrocarbon being present in an amount up to about 60 percent by weight based on the total amount of said resin and said hydrocarbon in the composition.

3. The composition of claim 2, wherein said hydrocarbon is mineral oil.

4. The composition of claim 2, wherein said hydrocarbon is present in an amount from about 20 to about 60 percent by weight based on the total amount of said resin and said hydrocarbon in the composition.

5. The composition of claim 4, wherein said mixture comprises about 40 to about 60 parts by weight of said resin and about 60 to about 40 parts by weight of said hydrocarbon.

6. The composition of claim 1, wherein said polyolefin has a density at 75° F. of about 0.8 to about 0.9, an iodine number of about 29 to about 31, and a viscosity at 37.8° C. of about 400 to about 1000 centistokes.

7. The composition of claim 6, wherein said density is about 0.84 to about 0.88, said iodine number is about 30 and said viscosity is about 530 centistokes.

8. The composition of claim 1, further comprising at least one coloring material.

9. The composition of claim 8, wherein the coloring material is selected from the group consisting of dyes, pigments, pearling agents and mixtures thereof.

10. The composition of claim 1, also containing at least one ingredient selected from the group consisting of perfumes, sunscreens, antioxidants and preservatives.

11. The composition of claim 8, also containing at least one ingredient selected from the group consisting of perfumes, sunscreens, antioxidants and preservatives.

12. The composition of claim 1, said composition comprising:
   (a) about 0.2 to about 2.0 parts by weight of said resin;
   (b) about 10 to about 25 parts by weight of said polysiloxane;
   (c) about 25 to about 40 parts by weight of said polyolefin; and
   (d) about 5 to about 30 parts by weight of at least one hardening agent.

13. The composition of claim 12, further containing up to about 40 parts by weight of coloring material and up to about 16 parts by weight of one or more ingredients selected from the group consisting of perfumes, sunscreens, antioxidants and preservatives.

14. The composition of claim 1, said composition comprising:
   (a) a combination of about 0.4 to about 2.0 parts by weight of (i) a resin having a softening point of about 100° C. to about 125° C., and (ii) a hydrocarbon that is liquid at room tempera- ture;
(b) about 10 to about 25 parts by weight of said polysiloxane;
(c) about 25 to about 40 parts by weight of said polyolefin; and
(d) about 5 to about 30 parts by weight of at least one hardening agent, said hardening agent comprising 0 to 100 percent by weight of Fischer-Tropsch wax with a melting point of about 72 to about 78° C. and 100 to 0 percent by weight of a mixture of microcrystalline waxes, said mixture of microcrystalline waxes having a melting point of about 75 to about 76° C.

15. The composition of claim 14, further comprising up to 40 parts by weight of a coloring material and up to 16 parts by weight of one or more ingredients selected from the group consisting of perfumes, sunscreens, antioxidants and preservatives.

16. The composition of claim 1, said composition comprising:
(a) about 0.75 to about 1.25 parts by weight of a resin, 1, said resin having a softening point of about 115° C., and mineral oil, the mineral oil being present in an amount from about 40 to about 60 percent by weight, based on the total amount of said mineral oil in the composition;
(b) about 14 to about 20 parts by weight of phenylmethylpolysiloxane having a viscosity of about 22.5 centistokes at 25° C.;
(c) about 30 to about 35 parts by weight of a polyolefin, said polyolefin having a viscosity of about 530 centistokes at 37.8° C., an iodine number of about 30, a pour point of less than −30° F., and a density at 75° F. of about 0.86;
(d) about 18 to about 24 parts by weight of a hardening agent, said hardening agent comprising a blend of about 40 to about 60 percent by weight of Fischer-Tropsch wax with a melting point of about 72 to about 78° C. and about 60 to about 40 percent by weight of a mixture of microcrystalline waxes having a melting point of about 75.5° C.;
(e) about 8 to about 12 parts by weight of pigment;
(f) about 14 to about 23 parts by weight of a pigment vehicle comprising squalane and octyl dodecanol; and
(g) about 0.1 to 1.5 parts by weight of one or more other ingredients selected from the group consisting of perfumes, sunscreens, antioxidants and preservatives.

17. The composition of claim 16, wherein said sunscreen is octyl dimethyl para-amino benzoic acid, said preservative comprises butyl paraben and propyl paraben, and said antioxidant is tocopherol.

18. The composition of claim 17, wherein said other ingredients also include hydrolyzed animal protein.

19. The composition of claim 16, wherein said resin is a polymer of dipentene.

20. A molded product in the shape of a lipstick made from the composition of claim 1.

21. A molded product in the shape of a lipstick made from the composition of claim 13.

22. A molded product in the shape of a lipstick made from the composition of claim 15.

23. A molded product in the shape of a lipstick made from the composition of claim 16.

24. A molded product in the shape of a lipstick made from the composition of claim 19.

* * * * *

UNITED STATES PATENT AND TRADEMARK OFFICE
CERTIFICATE OF CORRECTION

PATENT NO.  : 4,699,780
DATED       : October 13, 1987
INVENTOR(S) : Jennings et al.

It is certified that error appears in the above-identified patent and that said Letters Patent is hereby corrected as shown below:

Col. 5, Line 27, "oomposition" should be --composition--

Col. 7, Line 23, Before "lipstick" insert --A--

Col. 9, Line 2, "tempera- ture" should be --temperature--

Signed and Sealed this

Twenty-fifth Day of October, 1988

Attest:

DONALD J. QUIGG

Attesting Officer

Commissioner of Patents and Trademarks